United States Patent [19]
Agnello

[11] Patent Number: 6,096,498
[45] Date of Patent: *Aug. 1, 2000

[54] PROBE FOR DETECTING HEPATITIS C VIRUS IN TISSUES

[76] Inventor: Vincent Agnello, 11 French Rd., Weston, Mass. 02193

[*] Notice: This patent is subject to a terminal disclaimer.

[21] Appl. No.: 09/106,566

[22] Filed: Jun. 29, 1998

Related U.S. Application Data

[62] Division of application No. 08/414,441, Mar. 31, 1995, Pat. No. 5,830,635.

[51] Int. Cl.$^7$ .............................. C12Q 1/70; C12Q 1/68; C12P 19/34
[52] U.S. Cl. ................... 435/5; 435/6; 435/91.2
[58] Field of Search .............................. 435/4, 5, 6, 40.5, 435/91.2; 935/8, 77, 78; 536/23.7, 24.32, 24.33

[56] References Cited

U.S. PATENT DOCUMENTS

| | | | |
|---|---|---|---|
| 5,830,635 | 11/1998 | Agnello | 435/5 |
| 5,846,704 | 12/1998 | Maertens et al. | 435/5 |

FOREIGN PATENT DOCUMENTS

| | | | |
|---|---|---|---|
| 0516270A2 | 9/1992 | European Pat. Off. | 15/36 |

OTHER PUBLICATIONS

Han et al, Charaterization of the terminal region of Hepatitis C viral RNA: Identification of conserved sequences in the 5' untranslated region and poly(A) tails at the 3' end, Proc. Natl. Acad. Sci. Vol 88, pp 1711–1715, Mar. 1991, Biochemistry/.

Moldvay et al, Detection of Hepatitis C Virus RNA in Peripheral Blood Mononuclear Cells of Infected Patients by in Situ Hybridization, J. Am. Soc. Hemat., Vol 83, No. 1 (Jan. 1994) pp. 269–273.

Hu et al. Direct Detection of Circulating Hepatitis C Virus RNA Using Probes from the 5' Untranslated Region, J. Clin. Invest., vol. 89, Jun. 1992, pp. 2040–2045.

Lau et al, In Situ Detection of Heptits C virus—a critical appraisal—J. Hepat,,. 1996, Vol 24, (Supp 2) pp 43–51.

Nouri–Aria et al, Detection of Genomic and Intermediate Replicative Strands of Hepatitis C Virus in Liver Tissue by In Situ Hybridization, J. Clin. Invest. Vol 91, May 1993, pp. 2226–2234.

Negro et al. Detection of intrahepatic replication of hepatitis C virus RNA by in situ hybridization and comparison with histopathology, Proc. Natl Acad. Sci., vol. 89, Mar. 1992, pp. 2247–2251.

Arrand, Nucleic Acid Hybridization—a practical approach, ed, by Hames et al, IRL Press, Washington, D.C., 1985, pp. 42–45.

Lee et al, Identification of Hepatitis C Viruses with a Nonconserved Sequence in the 5' Untranslated Region J. Clin Microbiol., Vol 30, No. 6, Jun. 1992, pp. 1602–1604.

Bukh et al. Sequence analysis of the 5' noncoding region of hepatitis C virus, Proc. Natl. Acad. Sci Vol 89, pp 4942–4946 Jun. 1992, Biochemistry.

*Primary Examiner*—Lisa B. Arthur
*Assistant Examiner*—Jeanine Enewold
*Attorney, Agent, or Firm*—Robert J. Schiller

[57] ABSTRACT

A probe that is a labelled segment of RNA complementary to and capable of specifically hybridizing with denatured HCV RNA, and prepared from 5' sense, GGCGACACTC-CACCATGAAT and 3' antisense, ccagagcatctggcacgtgg primers, from the 5' untranslated region of the HCV genome, is employed for detecting and identifying the presence of hepatitis C virus (HCV) in tissue.

3 Claims, No Drawings

PROBE FOR DETECTING HEPATITIS C VIRUS IN TISSUES

This application is a divisional of U.S. application Ser. No. 08/414,441 filed Mar, 31, 1995, now U.S. Pat. No. 5,830,635.

This invention relates to hepatitis C virus and more particularly to a method of detecting the infection of tissue by hepatitis C virions.

Hepatitis C virus (hereinafter HCV) has been shown to be the major cause of acute and chronic post-transfusion and sporadic non-A, non-B hepatitis. In recent years, the cloning and sequencing of the HCV genome have resulted in assays for detecting markers of HCV infection. (Negro F., Pacchioni D., Shimtzu Y., et al. Detection of intrahepatic replication of hepatitis C virus RNA by in situ hybridization and comparison with histopathology. *Proc. Natl. Acad. Sci.* 1992;89:2247–2251; Nouri Aria KT., Sallie R., Sangar D., et al., Detection of genomic and intermediate replicative strands of hepatitis c virus in liver tissue by in situ hybridization. *J. Clin. Invest.*, 1993;91:2226–34).

In such assays, the probes employed were based on the 5' non-coding region of the HCV genome which was believed to be highly conserved although recently it has been established that the 5' non-coding region possesses significant heterogeneity among HCV isolates taken from patients at various locations around the world (Bukh J., Purcell R. H., Miller R. H., Sequence analysis of the 5' noncoding region of hepatitis C virus, *Proc. Natl. Acad. Sci. USA*, 1992;89:4942–4946).

A direct approach to delineating the role of HCV infection, for example in the pathogenesis of essential mixed cryoglobulinemia, is to determine whether complexes of viral antigen are present in the patient's tissues such as the pathologic lesions associated with this disease. HCV has not been propagated in culture nor visualized directly, but both the putative virion positive strand RNA and the putative replicative negative strand RNA are detectable by in situ hybridization in liver tissue. Thus, it is possible to deduce that active infection is present by detection of the negative strand HCV RNA.

An in situ hybridization procedure is one in which the hybridization occurs within tissues usually mounted on a microscope slide. After addition and hybridization of the specific nucleic acid probe, the presence within the tissue of complementary nucleic acid molecules, such as may be characteristic of an infectious agent or the like, can be detected with a suitably labeled probe. For example the probe can be labeled with an enzymatic reagent system such as one based on the binding between the biotin of the probe and avidin, a biotin-binding protein. In such case, a known biotin-avidin-alkaline phosphatase system or a known avidin horseradish peroxidase detection complex can be used to recognize and bind to the biotin of the nucleic acid probe. The presence of hybridized biotinylated probe is determined by the addition of hydrogen peroxide and aminoethylcarbazole. The peroxidase enzyme bound to the nucleic acid reacts with these reagents to yield a localized red-colored precipitate indicating a positive reaction. At the completion of this reaction cellular morphology is intact and the cellular location of the target RNA can be visualized with a light microscope at modest magnifications.

It is believed however, that the prior art techniques for detecting HCV infection in tissues by in situ hybridization, particularly in archival material (e.g. formalin fixed tissue embedded in paraffin) have been unable to establish the presence of HCV histologically except in liver tissue. For example, cf. *J. Clin. Invest.*, 1993;91:2226–34, supra, at 2231 where the authors note that, although the probe employed was successful in detecting the presence of HCV in liver tissue, they were unable to detect the replicative intermediate strand of HCV RNA in bile duct epithelium despite the bile duct damage seen in chronic HCV infection and the bile duct was within the liver.

A principal object of the present invention is therefore to provide a novel probe for and a method of detecting hepatitis C virions histologically in liver and other tissues. Other objects of the present invention will in part be obvious and will in part appear hereinafter. The invention accordingly comprises the method and the several steps and relation and order of one or more of such steps with respect to each of the others which are exemplified in the following detailed disclosure, and the scope of the application of which will be indicated in the claims. For a fuller understanding of the nature and objects of the present invention, reference should be had to the following detailed description.

Generally, the present invention comprises a method of detecting and identifying the presence of hepatitis C virus in tissue by forming a probe of a segment of synthetic RNA complementary to and capable of specifically hybridizing with denatured HCV RNA, in situ hybridization of the probe with the HCV RNA, and detecting and measuring the amount of the synthetic probe RNA hybridized with the complementary HCV RNA.

Critically, the probes of the present invention are prepared from 5' sense, ggcgacactccaccatgaat (SEQ ID NO: 1) and 3' antisense, ccagagcatctggcacgtgg (SEQ ID NO: 2) primers, to produce what is believed to be a 341 base pair product from the 5' untranslated region of the HCV genome. While the use of probes prepared from the 5' noncoding region of the HCV genome are known they have been, for example, 390 or 249 base pairs in length (*J. Clin. Invest.*, 1993;91:2226–34, supra), 241 base pairs (Ke-Quin H., Chang-Hong Y., Vierling J. M, Direct Detection of Circulating Hepatitis C Virus RNA Using Probes from the 5' Untranslated Region,) *J. Clin. Inv.*, 1992,89;240–2045), 251 and 158 base pair fragments (Chao-Hung L., Cheng C., Jinghong W., Lumeno, L., Identification of Hepatitis C Viruses with a Nonconserved Sequence of the 5' Untranslated Region, *J. Clin Microbio.*, 1992;30:1602–1604) or 49 base pairs (*Proc. Natl. Acad. Sci.* 1992;89:2247–2251, supra), and hence differ significantly from the probes of the present invention.

To prepare the probes of the present invention, HCV RNA (typically isolated from the serum of a patient with Type II cryoglobulinemia) is preferably amplified by reverse transcriptase-polymerase chain reaction (RT-PCR) with 5' sense, ggcgacactccaccatgaat (SEQ ID NO: 1) and 3' antisense, ccagagcatctggcacgtgg (SEQ ID NO: 2) primers, resulting in a 341 base pair product from the 5' untranslated region of the HCV genome. The PCR product is cloned, for example using pCRII plasmid, the RNA transcript containing a small amount of plasmid sequences. The recombinant plasmid pGBKLF1 is digested as with XhoI restriction endonuclease, and the antisense RNA probe is synthesized using typically SP6 RNA polymerase and digoxigenin-UTP (DIG-UTP, Boehringer Mannheim, Indianapolis, Ind.)

A digoxigenin-labeled sense RNA probe is produced by instead digesting the plasmid with, for example, HindIII restriction endonuclease, and the labeled RNA is the synthesized as with T7 RNA polymerase.

The probes of the present invention are employed in an in situ hybridization technique for the detection of HCV RNA in formalin-fixed paraffin-embedded tissue that permits investigation of archival specimens as described in the following examples:

EXAMPLE I

A patient, a 62-year-old man, was admitted to the Lahey Clinic in Burlington, Mass. in April 1991 because of cryoglobulinemia, palpable purpura, splenomegaly, and thrombocytopenia. This patient had a 20-year history of intermittent palpable purpura and a 14-year history of cryoglobulinemia and transient elevation of serum transaminase levels. No history of blood transfusions or illicit intravenous drug use was elicited. In 1979, palpable purpura recurred accompanied by painless cervical adenopathy. No fever, sweats, or weight loss had occurred. Lymph node examination showed "areas of effacement of strands and sheet of neoplastic-appearing cells that was interpreted as strongly suggesting the emergence of a poorly differentiated diffuse lymphoma." Bone marrow biopsy showed no evidence of lymphoma. Computed tomography and lymphangiography showed diffuse lymphadenopathy. Stage 3 poorly differentiated diffuse lymphoma was diagnosed. Chemotherapy with streptonigrin, vincristine, and prednisone followed by cyclophosphamide, vincristine, and prednisone as maintenance therapy was given over 24 months and resulted in complete resolution of the lymphadenopathy and cutaneous vasculitis.

On admission to the Lahey Clinic, the cryocrit was 4 percent. Analysis of the cryoglobulin showed a Type II cryoglobulinemia with $IgM_k$ rheumatoid factors. Results of hepatitis B virus serologies were negative. Hepatitis C antibody was positive. Other pertinent abnormal laboratory studies were platelet count, 107,000/$\mu$l; serum glutamic-oxaloacetic transaminase, 141 IU/L; alkaline phosphatase, 166 IU/L; bilirubin, 1.8 mg/dl; $CH_{50}$, 62 U (normal, 150–250 U); $C_3$, 65 mg/dl and $C_4$,<4 mg/dl. Results of antinuclear antibody, antimicrosomal, and antimitochondrial antibody tests were negative. Liver biopsy showed fatty metamorphosis, focal hepatocellular necrosis, and portal chronic inflammation. Skin biopsy showed leukocytoclastic vasculitis.

Proteinuria and microhematuria that developed during the hospital course were associated with a rise in serum creatinine from 0.8 to 2.5 mg/dl. Plasmapheresis therapy resulted in rapid onset of ascites and edema, which resolved with diuretic therapy. Treatment with alpha interferon, 3 million units subcutaneously three times a week, was begun, and the patient returned home. Palpable purpura resolved within 2 weeks. Over the next 4 weeks, the cryocrit fell to 1 percent, and the platelet count, serum transaminases, alkaline phosphatase, bilirubin, and creatinine returned to normal levels.

Formalin-fixed, paraffin-embedded lymph node and biopsy specimens of skin and liver from this patient were used for immunohistologic and in situ hybridization studies. Routine immunoperoxidase techniques were used for detection of IgG, IgM, $\lambda$ and $\kappa$ light chains, and T and B cell markers. The method previously described for detection of intracytoplasmic WA monoclonal rheumatoid factor (MRF) was adapted to the immunoperoxidase technique and used to study the lymph node specimen.

In situ hybridization was performed using deparaffinized 4.5 $\mu$m sections on silanized glass slides. Sections were digested with proteinase K (Sigma Diagnostics, St. Louis, Mo.), 0.2 mg/ml in PBS for 15 minutes at 37° C., washed with PBS, denatured for 5 minutes at 65° C. in 70 percent formamide, 0.1×SSC, and prehybridized at room temperature for 1 hour in 50 percent formamide, 0.3 M NaCl, 20 mM Tris-HCl, pH=7.4, 5 MM EDTA, 10 mM NaPO4, pH=8.0, 1×Denhardt's solution, 10 percent dextran sulfate, and 50 $\mu$g/ml yeast tRNA. Hybridization was performed using 15 to 20 ng of either riboprobe at 52° C. for 16 hours in a humid chamber. Slides were then washed at 60° C. for 5 minutes in 50 percent formamide, 2×SSC, and 0.1 M dithiothreitol, and treated with RNase One (Promega, Madison, Wis.) in washing buffer for 45 minutes at 37° C. Slides were washed at 37° C. in 2×SSC, then in 0.1×SSC (15 minutes each), and then briefly in Tris-NaCl buffer (100 mM Tris-HCl, pH=7.5, 150 mM NaCl). The hybridized digoxigenin-labeled probes were detected with the Genius 3 Nucleic acid detection kit (Boehringer Mannheim, Indianapolis, Ind.) using either alkaline phosphatase-conjugated antidigoxigeninantibody and 5-bromo-4-chloro-3-indolyl phosphate chromogen or horseradish peroxidase-conjugated antidigoxigenin antibody and enhanced diaminobenzidine chromogen. The slides were counterstained with 1.0 percent methyl green.

In situ hybridization for hepatitis B virus (HBV) was performed using the Pathogene DNA probe assay kit for HBV (ENZO Diagnostics, Syosset, N.Y.).

Previous studies (Agnello V, Chung RT, Kaplan LE. A role for hepatitis C virus infection in Type II cryoglobulinemia. N. Eng. J. Med 1992;327:1490–5) had demonstrated that the patient had both HCV antibodies and HCV RNA concentrated in the cryoglobulins along with the typical WA mRF found in Type II cryoglobulins. In this example, the positive strand HCV RNA was demonstrated in a biopsy of the patient's palpable purpura lesion; only scant amounts of the negative strand RNA were present. The HCV RNA was detected mainly in the adventitia. Similar results were obtained with two other biopsies of palpable purpura lesions from other HCV-positive patients with Type II cryoglobulinemia. A biopsy of unaffected skin from a patient with HCV-positive skin lesions was negative, as were three control biopsies of normal skin and four control biopsies of skin lesions from HCV-negative patients with other types of cutaneous vasculitis (three patients with allergic cutaneous vasculitis and one patient with polyarteritis nodosa). In contrast to the results of skin biopsy, the liver biopsy in this patient showed greater amounts of the replicative form of the hepatitis C virus that appeared to be in the cytoplasm of hepatocytes. Similar results were obtained with biopsies from four HCV-positive patients with chronic active hepatitis. Prehybridization RNase treatment of the liver section or blocking with the same unlabeled riboprobe eliminated staining. All five biopsies were negative for HBV by in situ hybridization. Two biopsies from HBV-positive, HCV-negative patients with chronic hepatitis that were positive for HBV by in situ hybridization were negative for HCV, demonstrating the specificity of HCV in situ hybridization technique of the present invention.

EXAMPLE II

A lymph node specimen, obtained in 1979 from a patient who had been diagnosed as having lymphoma and Type II cryoglobulinemia 12 years before the detection of HCV infection, was examined for the presence of HCV to determine whether infection had been present at the time the diagnosis of lymphoma was made. Histologic examination of this 14-year-old lymph node specimen showed effacement of normal architecture with a polymorphous population of lymphoid cells with mild cytologic atypia not diagnostic for lymphoma. Immunohistologic studies were suboptimal but showed approximately the following cell distribution: B cell to T cell ratio of 1:1, IgM to IgG ratio of 2.5:1, and K to X ratio of 1.5:1. There was no area of the node where there were exclusively B cells or IgM cells on K light chain cells. Studies to detect WA mRF were negative. Using the probes of the present invention to effect in situ hybridization, both positive strand RNA and the replicative form of the virus were detected in about equal amounts in the lymph node and appeared to be located in the cytoplasm. The type of cells containing virus could not be identified.

EXAMPLE III

Two lymph node biopsies from HCV-negative patients with lymphoma were negative for both forms of HCV. Two lymph node biopsy specimens, 9 years old and 12 years old, respectively, from patients with lymphoma (patients' sera were unavailable for HCV testing) were also negative for HCV.

The above examples indicate that HCV infection in a patients with type II cryoglobulinemia involve skin, liver, and lymph nodes. It appears that in the skin predominantly the putative virion form of the virus was deposited in the adventitia of inflamed vessels, whereas in the liver, the putative replicative form of the virus indicating active infection was present in addition to the virion form. The presence of the replicative form of the virus in the 14-year-old lymph node specimen indicates active infection of the node and at least a 14-year chronic infection associated with the manifestation of Type II cryoglobulinemia. Attempts to demonstrate the WA mRF in the lymph node were unsuccessful; however, it is known that WA crossidiotype is labile and most likely would have been destroyed by formalin fixation if present. It is believed that this is the first histologic demonstration of HCV in a cutaneous vasculitis lesion and lymph node in a patient with Type II cryoglobulinemia. A letter reporting the use of PCR assays for HCV RNA from extracted tissue, describes a method that does not distinguish intravascular from tissue HCV. (Durand JM, Kaplanski G, Richard MA, et al. Cutaneous vasculitis in a patient infected with hepatitis C virus. Detection of hepatitis C virus RNA in the skin by polymerase chain reaction. *Br. J. Dermatol.* 1993;128:359–60 (letter).

Since certain changes may be made in the above method without departing from the scope of the invention herein involved, it is intended that all matter contained in the above description or shown in the accompanying drawings shall be interpreted in an illustrative and not in a limiting sense.

What is claimed is:

1. A probe for detecting and identifying the presence of hepatitis C virus (HCV) in tissue, said probe being a segment of RNA complementary to and capable of specifically hybridizing with denatured HCV RNA in said tissue, and being formed from the 5' untranslated region of the HCV genome by amplification of the HCV RNA with primers of SEQ ID NO. 1 and SEQ ID NO. 2.

2. A probe as defined in claim 1 wherein said probe is labelled with a reagent that will produce a signal responsively to hybridization of said probe with said denatured HCV RNA.

3. A probe as defined in claim 2 wherein said reagent is an enzyme.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

GGCGACACTC CACCATGAAT    20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:2:

CCAGAGCATC TGGCACGTGG    20